United States Patent
Lee et al.

(10) Patent No.: US 10,022,317 B2
(45) Date of Patent: Jul. 17, 2018

(54) COMPOSITION COMPRISING AN EXTRACT OF HERBAL MEDICINE PROCESSED BY AN ORIENTAL HERBAL MEDICINE PROCESSING

(71) Applicant: AMOREPACIFIC CORPORATION, Seoul (KR)

(72) Inventors: Ok Chan Lee, Yongin-si (KR); Dong Hyun Kim, Yongin-si (KR); Kyeong Hwan Hwang, Yongin-si (KR); Myeong Hun Yeom, Yongin-si (KR); Jun Cheol Cho, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 60 days.

(21) Appl. No.: 14/894,234

(22) PCT Filed: May 30, 2014

(86) PCT No.: PCT/KR2014/004830
§ 371 (c)(1),
(2) Date: Nov. 25, 2015

(87) PCT Pub. No.: WO2014/193185
PCT Pub. Date: Dec. 4, 2014

(65) Prior Publication Data
US 2016/0101042 A1   Apr. 14, 2016

(30) Foreign Application Priority Data

May 31, 2013 (KR) .................. 10-2013-0062374

(51) Int. Cl.
| | |
|---|---|
| *A61K 36/00* | (2006.01) |
| *A61K 8/97* | (2017.01) |
| *A61K 36/82* | (2006.01) |
| *A61K 36/258* | (2006.01) |
| *A61Q 19/00* | (2006.01) |
| *A61Q 19/08* | (2006.01) |

(52) U.S. Cl.
CPC .............. *A61K 8/97* (2013.01); *A61K 36/258* (2013.01); *A61K 36/82* (2013.01); *A61Q 19/007* (2013.01); *A61Q 19/08* (2013.01); *A61K 2800/596* (2013.01); *A61K 2800/5922* (2013.01); *A61K 2800/70* (2013.01); *A61K 2800/805* (2013.01)

(58) Field of Classification Search
CPC ...................................................... A61K 36/00
See application file for complete search history.

(56) References Cited

FOREIGN PATENT DOCUMENTS

| | | |
|---|---|---|
| JP | 2011519850 | 7/2011 |
| KR | 1020010035409 A | 5/2001 |
| KR | 1020090056296 A | 6/2009 |
| KR | 1020110098124 A | 9/2011 |
| KR | 1020110131784 A | 12/2011 |
| KR | 2012132843 A * | 12/2012 |
| KR | 1020130048282 A | 5/2013 |
| KR | 1020140049341 A | 4/2014 |
| WO | 2009133998 | 11/2009 |

OTHER PUBLICATIONS

International Search Report with English Translation for International Application No. PCT/KR2014/004830 dated Sep. 12, 2014.
Written Opinion for International Application No. PCT/KR2014/004830 dated Sep. 12, 2014.
Japanese Office Action—Japanese application No. 2016-516452 dated Mar. 9, 2018.
Japanese pre-symptomatic system society magazine, vol. 13, pp. 256-259.

* cited by examiner

*Primary Examiner* — Qiuwen Mi
(74) *Attorney, Agent, or Firm* — Cantor Colburn LLP

(57) ABSTRACT

The present specification relates to a composition comprising processed ginseng extract and processed green tea extract. Such a composition results in having a synergistic effect due to mixing of each processed extract, and is thus capable of promoting the production of procollagen and inhibiting the expression of collagenase. In addition, the composition of the present specification promotes the expression of filaggrin and is thus capable of strengthening a skin barrier function and inducing the differentiation of skin keratinocytes. Therefore, the composition of the present specification is capable of improving the general condition of skin, and can be effectively used as an external preparation for skin for preventing or improving xeroderma, atopic dermatitis, contact dermatitis, psoriasis, or the like that is caused by the imperfection of epidermal differentiation.

8 Claims, No Drawings

COMPOSITION COMPRISING AN EXTRACT OF HERBAL MEDICINE PROCESSED BY AN ORIENTAL HERBAL MEDICINE PROCESSING

TECHNICAL FIELD

The present disclosure relates to a composition comprising a ginseng extract and a green tea extract which are processed by an oriental herbal medicine processing.

BACKGROUND ART

The external appearance of skin is determined by the extracellular matrix (ECM) in the dermal tissue. Collagen accounts for about 70-80% of the proteins present in the ECM. The formation of skin wrinkles is caused by the inhibited production and degradation of collagen induced by aging, UV, etc. In particular, the expression of matrix metalloproteinases such as collagenase leads to wrinkle formation via breakdown of collagen that has been normally produced in skin.

Various substances have been developed and are used to inhibit the reduction of collagen which causes wrinkle formation. Retinoids such as retinol, retinoic acid, etc. exhibit the effect of improving wrinkles (*Dermatologic Therapy*, 1998, 16, 357-364) and a composition comprising malt extract is used to inhibit collagenase. However, the retinoids are disadvantageous in that they can cause irritation when applied to skin even with a small amount. And, since substances derived from natural products have been mostly used as simple extracts and it is unclear what ingredients of the extracts exhibit the desired effect, it is difficult to continuously maintain and control the activity of the extracts.

Decreased water content in skin often leads cornification caused by skin dryness. Also, it results in loss of skin luster, easy formation of fine wrinkles and early skin aging. Accordingly, skin moisturization is essential for improvement of skin.

The inventors of the present disclosure have found out that a mixture of a oriental herbal medicine processed ginseng extract and a oriental herbal medicine processed green tea extract exhibits very superior synergic effect in prevention of skin wrinkle formation, improvement of wrinkles and moisturization of skin as compared to a mixture of simple ginseng and green tea extracts.

DISCLOSURE

Technical Problem

The present disclosure is directed to providing a composition comprising a oriental herbal medicine processed extract of natural products.

Technical Solution

In a general aspect, the present disclosure provides a composition comprising a mixture of a oriental herbal medicine processed ginseng extract and a oriental herbal medicine processed green tea extract.

Advantageous Effects

A composition of the present disclosure, which comprises a mixture of a oriental herbal medicine processed ginseng extract and a oriental herbal medicine processed green tea extract, exhibits remarkably superior anti-aging effect or moisturizing effect as compared to a mixture of unprocessed extracts or each of the oriental herbal medicine processed extracts alone. Specifically, owing to the synergic effect resulting from the mixing of the oriental herbal medicine processed extracts, the composition of the present disclosure can promote the production of procollagen and inhibit the expression of collagenase. In addition, by promoting the expression of filaggrin, the composition of the present disclosure can enhance skin barrier function and induce the differentiation of skin keratinocytes. Furthermore, since the composition of the present disclosure comprises only natural extracts, it exhibits little toxicity or irritation and has few side effects even after long-term use.

Accordingly, the composition of the present disclosure can be usefully used as a composition for external application to skin, which can improve the overall condition of skin and prevent or improve xeroderma, atopic dermatitis, contact dermatitis, psoriasis, etc. caused by incomplete epidermal differentiation.

BEST MODE

Korean Patent Application No. 10-2013-0062374, which was filed on May 31, 2013 is incorporated herein in its entirety for all purposes. In addition, this application claims the priority of Korean Patent Application No. 10-2013-0062374 and all the benefits accruing therefrom, the contents of which in its entirety are herein incorporated by reference.

In an aspect, the present disclosure relates to a composition comprising a mixture of a oriental herbal medicine processed ginseng extract and a oriental herbal medicine processed green tea extract.

In an exemplary embodiment of the present disclosure, the composition may be a composition for external application to skin.

In an exemplary embodiment of the present disclosure, the composition may be a composition for skin anti-aging, comprising a mixture of a oriental herbal medicine processed ginseng extract and a oriental herbal medicine processed green tea extract as an active ingredient.

In an aspect, the present disclosure relates to a method for skin anti-aging, which includes administering a mixture of an oriental herbal medicine processed ginseng extract and an oriental herbal medicine processed green tea extract to a subject in need of skin anti-aging. Specifically, in an exemplary embodiment of the present disclosure, the administration may follow the administration method or administration dose described in the present disclosure.

In an aspect, the present disclosure relates to a use of an oriental herbal medicine processed ginseng extract and an oriental herbal medicine processed green tea extract for skin anti-aging.

In an aspect, the present disclosure relates to an oriental herbal medicine processed ginseng extract and an oriental herbal medicine processed green tea extract for use in skin anti-aging.

In an exemplary embodiment of the present disclosure, the mixture of a oriental herbal medicine processed ginseng extract and a oriental herbal medicine processed green tea extract includes not only an extract of a mixture of ginseng and green tea but also a mixture of a ginseng extract and a green tea extract, which have been extracted separately.

In the present disclosure, the term "oriental herbal medicine processing" refers to a method of processing a herbal medicine based on the traditional medical knowledge to change the inherent properties of the medicine. The oriental herbal medicine processing may include boiling, steaming, roasting, parching or heating to reduce toxicity, maintain or enhance nature or improve convenience of taking. For example, the oriental herbal medicine processing methods include roasting herbal medicine, parching herbal medicine together with a liquid supplementary material such that the supplementary material permeates into the medicine, steaming herbal medicine together with a liquid supplementary material in a suitable container and/or drying to a desired extent, or the like. The processing methods are further subdivided according to the intensity of fire used and the supplementary material used. Several examples are as follows. Roasting is a method of roasting herbal medicine with fire with mild flame or intense flame to a prescribed state. Wine parching is a method of parching herbal medicine with about 15% alcohol and liquor steaming is a method of steaming herbal medicine using about 15% alcohol. Even the same herb often shows difference in nature and function in live state and processed state. A combination prescription of live and processed herbs may provide an effect of enhancing the efficacy of each herbal medicine or may maximize therapeutic effect by counteracting toxicity.

In the present disclosure, the term "oriental herbal medicine processed" means green tea or ginseng pretreated by the above-defined "oriental herbal medicine processing". Specifically, the oriental herbal medicine processing may be steaming or parching, but is not limited thereto. Specifically, in the present disclosure, the "oriental herbal medicine processed" green tea or ginseng may be obtained by a) oriental herbal medicine processing green tea or ginseng at high temperature and high pressure; and b) drying the oriental herbal medicine processed green tea or ginseng. However, any processing method commonly employed in the art may be used without being limited thereto.

In the present disclosure, the term "salt parching" refers to a method of parching herbal medicine while or after treating with brine. For example, the herbal medicine may be parched after being immersed in brine or the herbal medicine may be parched to a predetermined extent and, after spraying brine, may be parched again, although not being limited thereto. Sun-dried salt, rock salt, refined salt, processed salt or bamboo salt may be used. However, without being limited thereto, any commonly available salt may be used.

In the present disclosure, the term "scorching" is one of the methods of roasting herbal medicine. For example, it includes a method of roasting herbal medicine to a state where the outside is black and the inside is brown or yellowish-brown, although not being limited thereto.

In the present disclosure, the term "vinegar parching" refers to a method of parching herbal medicine while or after treating with vinegar. For example, the herbal medicine may be parched after being soaked in rice vinegar or it may be pulverized, parched and, when the surface becomes glossy or the stink disappears, parched while spraying rice vinegar, although not being limited thereto. The vinegar may be brewed vinegar, grain vinegar, fruit vinegar or synthetic vinegar. However, without being limited thereto, any commonly available vinegar may be used.

In the present disclosure, the term "liquor steaming" refers to a method of steaming herbal medicine with liquor. For example, the herbal medicine may be steamed after being mixed with huangjiu (yellow wine), although not being limited thereto. The liquor includes brewed beverage, distilled beverage, cocktail, huangjiu, rice wine, etc., but is not limited thereto.

In the present disclosure, the term "ginger parching" refers to a method of parching or boiling herbal medicine while or after treating with ginger juice. For example, the herbal medicine may be parched after being soaked in ginger juice or may be boiled with sliced ginger and then dried after the boiled ginger juice is completely absorbed, although not being limited thereto. The ginger may be one which is commonly available.

In the present disclosure, the term "honey parching" refers to a method of parching herbal medicine while or after treating with honey. For example, the herbal medicine may be parched after being mixed with refined honey until the honey is immersed into the herbal medicine. Alternatively, the herbal medicine may be parched and, after adding refined honey, then parched while stirring quickly. The refined honey refers to honey obtained by boiling with gentle heat until the moisture disappears. The honey may be acacia honey, canola honey or traditional honey. However, without being limited thereto, any commonly available honey may be used.

In the present disclosure, the "ginseng" may be any ginseng, dried or undried, regardless of its kind or age. In the present disclosure, the ginseng may be any part of ginseng. Specifically, root may be used.

In the present disclosure, the "green tea" may be any green tea, dried or undried, regardless of its kind or age. In the present disclosure, the green tea may be any part of green tea. Specifically, leaf may be used.

In the present disclosure, the term "anti-aging" includes inhibition or alleviation of freckles, live spots or lentigo, inhibition or alleviation of skin wrinkles, improvement of skin wrinkles or retardation or alleviation of biological change with time.

A composition according to an exemplary embodiment of the present disclosure comprises a 'oriental herbal medicine processed' green tea extract and a 'oriental herbal medicine processed' ginseng extract and exhibits remarkably superior anti-aging effect as compared to a general mixture of a green tea extract and a ginseng extract.

In an exemplary embodiment of the present disclosure, the composition may inhibit formation of skin wrinkles or improve skin wrinkles. In an exemplary embodiment of the present disclosure, the composition may inhibit skin wrinkle formation or improve skin wrinkles by promoting the production of procollagen and inhibiting the expression of collagenase.

In an aspect, the present disclosure may relate to a method for inhibiting formation of skin wrinkles or improving skin wrinkles, which includes administering a mixture of an oriental herbal medicine processed ginseng extract and an oriental herbal medicine processed green tea extract to a subject in need of inhibiting formation of skin wrinkles or improving skin wrinkles.

In an aspect, the present disclosure may relate to a use of a mixture of an oriental herbal medicine processed ginseng extract and an oriental herbal medicine processed green tea extract for inhibiting formation of skin wrinkles or improving skin wrinkles.

In an aspect, the present disclosure may relate to a mixture of an oriental herbal medicine processed ginseng extract and an oriental herbal medicine processed green tea extract for use in inhibiting formation of skin wrinkles or improving skin wrinkles.

In an exemplary embodiment of the present disclosure, the composition may inhibit the expression of collagenase.

In an exemplary embodiment of the present disclosure, the composition may be a composition for moisturizing skin, which comprises a mixture of a oriental herbal medicine processed ginseng extract and a oriental herbal medicine processed green tea extract as an active ingredient. The composition according to an exemplary embodiment of the present disclosure may increase water content in skin by promoting the expression of filaggrin in keratinocytes and may maintain the skin moisturizing effect even after a long period of time after treating with the composition.

In an aspect, the present disclosure may relate a method for moisturizing skin, which includes administering a mixture of an oriental herbal medicine processed ginseng extract and an oriental herbal medicine processed green tea extract to a subject in need of moisturizing skin.

In an aspect, the present disclosure may relate a use of a mixture of an oriental herbal medicine processed ginseng extract and an oriental herbal medicine processed green tea extract for moisturizing skin.

In an aspect, the present disclosure may relate a mixture of an oriental herbal medicine processed ginseng extract and an oriental herbal medicine processed green tea extract for use in moisturizing skin.

The composition according to the present disclosure, which comprises the 'oriental herbal medicine processed' green tea extract and the 'oriental herbal medicine processed' ginseng extract, exhibits remarkably superior moisturizing effect as compared to a general mixture of a green tea extract and a ginseng extract owing to a synergic effect.

In an exemplary embodiment of the present disclosure, the composition may enhance skin barrier function and induce the differentiation of keratinocytes in skin. Accordingly, it can be usefully used as a composition for external application to skin which prevents or improves xeroderma, atopic dermatitis, contact dermatitis, psoriasis, etc. caused by incomplete epidermal differentiation.

In an exemplary embodiment of the present disclosure, the oriental herbal medicine processed ginseng extract may comprise ginseng polysaccharide.

In an exemplary embodiment of the present disclosure, the ginseng polysaccharide may be one or more selected from a group consisting of salt-parched ginseng polysaccharide, scorched ginseng polysaccharide, vinegar-parched ginseng polysaccharide, liquor-steamed ginseng polysaccharide, ginger-parched ginseng polysaccharide and honey-parched ginseng polysaccharide.

In the present disclosure, the term "ginseng polysaccharide" refers to a pectin-like polysaccharide with a molecular weight of about 34,600, consisting of mostly galacturonic acid (about 60%) and arabinose, rhamnose, glucose, galactose, etc. as appendant residues.

In an exemplary embodiment of the present disclosure, the oriental herbal medicine processed green tea extract may comprise green tea polysaccharide.

In the present disclosure, the term "green tea polysaccharide" refers to a polysaccharide derived from green tea, which is an acidic polysaccharide different from those found in other plants. It is produced from the binding between a sugar which is a photosynthesis product and an amino acid.

In an exemplary embodiment of the present disclosure, the green tea polysaccharide may be one or more selected from a group consisting of salt-parched green tea polysaccharide, scorched green tea polysaccharide, vinegar-parched green tea polysaccharide, liquor-steamed green tea polysaccharide, ginger-parched green tea polysaccharide and honey-parched green tea polysaccharide.

The polysaccharide of the present disclosure may be prepared according to a method known in the art, without particular limitation. Specifically, the ginseng or green tea polysaccharide may be obtained by extracting ginseng or green tea leaf at 38-42° C., concentrating the resulting extract, removing impurities through filtration, adding ethanol in a dropwise manner, and drying the product with hot air.

In the present disclosure, the salt-parched ginseng or green tea polysaccharide may be obtained by mixing ginseng or green tea leaf with brine, parching the resulting mixture at 100-180° C. for 10 minutes to 1 hour, extracting and concentrating the same, removing impurities through filtration, adding ethanol in a dropwise manner, and drying the product.

In the present disclosure, the scorched ginseng or green tea polysaccharide may be obtained by carbonizing the outside of ginseng or green tea leaf at 230-300° C., cooling, extracting and concentrating the same, removing impurities through filtration, adding ethanol in a dropwise manner, and drying the product.

In the present disclosure, the vinegar-parched ginseng or green tea polysaccharide may be obtained by soaking ginseng or green tea leaf in vinegar, parching the same at 100-160° C. for 10 minutes to 1 hour, drying, extracting and concentrating the same, removing impurities through filtration, adding ethanol in a dropwise manner, and drying the product.

In the present disclosure, the liquor-steamed ginseng or green tea polysaccharide may be obtained by immersing ginseng or green tea leaf in liquor and steaming for 30 minutes to 2 hours, drying, extracting and concentrating the same, removing impurities through filtration, adding ethanol in a dropwise manner, and drying the product.

In the present disclosure, the ginger-parched ginseng or green tea polysaccharide may be obtained by spraying ginger juice to ginseng or green tea leaf, parching the same at 100-180° C. for 10 minutes to 1 hour, drying, extracting and concentrating the same, removing impurities through filtration, adding ethanol in a dropwise manner, and drying the product.

In the present disclosure, the honey-parched ginseng or green tea polysaccharide may be obtained by soaking ginseng or green tea leaf in honey, parching the same at 100-160° C. for 10 minutes to 1 hour, drying, extracting and concentrating the same, removing impurities through filtration, adding ethanol in a dropwise manner, and drying the product.

In an exemplary embodiment of the present disclosure, a weight ratio of the oriental herbal medicine processed ginseng extract and the oriental herbal medicine processed green tea extract may be 0.1-10:1. The synergic effect of the two ingredients may be maximized at this weight ratio. More specifically, the weight ratio of the oriental herbal medicine processed ginseng extract and the oriental herbal medicine processed green tea extract may be 0.5-9.5:1, 1-9:1 or 1.5-8.5:1.

In an exemplary embodiment of the present disclosure, the composition may comprise 0.001-10 wt % of the oriental herbal medicine processed ginseng extract and the oriental herbal medicine processed green tea extract, respectively, based on the total weight of the composition. If the content of the extract is less than 0.001 wt %, the effect of improving skin wrinkles and moisturizing may be slight. And, the desired effect is not significantly increased even if the content exceeds 10 wt %. More specifically, the composition of the present disclosure may comprise 0.005-9.5 wt %, 0.01-9 wt %, 0.03-8.5 wt %, 0.05-8 wt %, 0.07-7.5 wt %, 0.09-7 wt %, 0.1-6.5 wt %, 0.3-6 wt %, 0.5-5.5 wt % or 0.7-5 wt % of the oriental herbal medicine processed ginseng extract and the oriental herbal medicine processed green tea extract, respectively, based on the total weight of the composition.

In an exemplary embodiment of the present disclosure, the composition may be a cosmetic composition.

The cosmetic composition according to the present disclosure may be provided in any formulation suitable for topical application. For example, it may be provided in the form of solution, oil-in-water emulsion, water-in-oil emulsion, suspension, solid, gel, powder, paste, foam or aerosol. Such formulations may be prepared according to methods commonly employed in the art.

The cosmetic composition according to the present disclosure may further comprise other ingredients that may provide a synergic effect to the main effect within a range not negatively affecting the main effect. Also, the cosmetic composition according to the present disclosure may further comprise a moisturizer, an emollient, a UV absorbent, a preservative, a disinfectant, an antioxidant, a pH control agent, an organic or inorganic pigment, a fragrance, a cooling agent or a deodorant. The addition amount of these ingredients may be easily determined by those skilled in the art within a range not negatively affecting the purpose and effect of the present disclosure. Specifically, they may be included in an amount of 0.01-5 wt %, more specifically 0.01-3 wt %, based on the total weight of the composition.

In an exemplary embodiment of the present disclosure, the composition may be a pharmaceutical composition.

The pharmaceutical composition according to the present disclosure may be prepared into formulations for oral or parenteral administration in solid, semisolid or liquid state by adding a commonly used inorganic or organic carrier to the active ingredient.

The formulations for oral administration may include tablet, pill, granule, capsule, powder, fine powder, dust, emulsion, syrup, pellet, etc. And, the formulations for parenteral administration may include injection, drop, ointment, lotion, spray, suspension, emulsion, suppository, etc. The formulations may be prepared easily according to commonly employed methods and a surfactant, a excipient, a colorant, a fragrance, a preservative, a stabilizer, a buffer, a suspending agent or other commonly used adjuvants may be used appropriately.

The pharmaceutical composition according to the present disclosure may be administered orally or parenterally, e.g., rectally, topically, transdermally, intravenously, intramuscularly, intraperitoneally, subcutaneously, etc.

The administration dose of the active ingredient of the pharmaceutical composition will vary depending on the age, sex and body weight of a subject, pathological condition and severity thereof, administration route or discretion of a diagnoser. Determination of the administration dose based on these factors is within the level of those skilled in the art. A daily administration dose may be, for example, 0.1-100 mg/kg/day, more specifically 5-50 mg/kg/day, although not being limited thereto.

Hereinafter, the present disclosure will be described in detail through examples. However, the following examples are for illustrative purposes only and it will be apparent to those of ordinary skill in the art that the scope of the present disclosure is not limited by the examples.

[Comparative Example 1] Preparation of Ginseng Polysaccharide 1 kg of dried white ginseng was pulverized using a mixer. After adding 10 L of purified water and extracting with warm water at 40° C. for 24 hours while stirring, the resulting extract was settled at 15° C. for a day. Then, after filtering through filter cloth and centrifuging, the residue and the filtrate were separated. The separated filtrate was concentrated under reduced pressure to 1/10 the volume of the purified water. Then, after adding ethanol of 4 times the volume of the concentrate in a dropwise manner, the product was dried with hot air to obtain 65 g of ginseng polysaccharide.

[Comparative Example 2] Preparation of Green Tea Polysaccharide 1 kg of primarily processed (panned) green tea leaf was pulverized using a mixer. After adding 10 L of purified water and extracting with warm water at 40° C. for 24 hours while stirring, the resulting extract was settled at 15° C. for a day. Then, after filtering through filter cloth and centrifuging, the residue and the filtrate were separated. The separated filtrate was concentrated under reduced pressure to 1/10 the volume of the purified water. Then, after adding ethanol of 4 times the volume of the concentrate in a dropwise manner, the product was dried with hot air to obtain 72 g of green tea polysaccharide.

[Comparative Example 3] Preparation of Oriental Herbal Medicine Processed Ginseng Extract Comprising Ginseng Polysaccharide (Red Ginseng Polysaccharide)

Undried fresh ginseng was steamed at 97° C. in a pressurized vessel for about 4 hours. The steamed fresh ginseng was dried with hot air at 65° C. and 1 kg of the oriental herbal medicine processed ginseng was pulverized using a mixer. After adding 10 L of purified water and extracting with warm water at 40° C. for 24 hours while stirring, the resulting extract was settled at 15° C. for a day. Then, after filtering through filter cloth and centrifuging, the residue and the filtrate were separated. The separated filtrate was concentrated under reduced pressure to 1/10 the volume of the purified water. Then, after adding ethanol of 4 times the volume of the concentrate in a dropwise manner, the product was dried with hot air to obtain 70 g of oriental herbal medicine processed ginseng polysaccharide (red ginseng polysaccharide).

[Comparative Example 4] Preparation of Oriental Herbal Medicine Processed Green Tea Extract Comprising Green Tea Polysaccharide Primarily processed (panned) green tea leaf was steamed at 97° C. in a pressurized vessel for about 4 hours. The steamed green tea leaf was dried with hot air at 65° C. and 1 kg of the processed green tea leaf was pulverized using a mixer. After adding 10 L of purified water and extracting with warm water at 40° C. for 24 hours while stirring, the resulting extract was settled at 15° C. for a day. Then, after filtering through filter cloth and centrifuging, the residue and the filtrate were separated. The separated filtrate was concentrated under reduced pressure to 1/10 the volume of the purified water. Then, after adding ethanol of 4 times the volume of the concentrate in a dropwise manner, the product was dried with hot air to obtain 70 g of oriental herbal medicine processed green tea polysaccharide.

[Comparative Example 5] Preparation of Mixture of Ginseng Extract and Green Tea Extract The ginseng polysaccharide prepared in Comparative Example 1 and the green tea polysaccharide prepared in Comparative Example 2 were mixed simply at a ratio of 1:1.

[Example 1] Preparation of Salt-Parched Mixed Polysaccharide 50 wt % of dried ginseng and 50 wt % of primarily processed (panned) green tea were mixed well with brine (2-3%) and allowed to stand under seal until the brine was completely absorbed. The resulting mixture of ginseng and green tea was parched at 140° C. for 40 minutes and then dried in the shade. 1 kg of the oriental herbal medicine processed mixture of ginseng and green tea was pulverized using a mixer. After adding 10 L of purified water and extracting 3 times under reflux, the resulting extract was settled at 15° C. for a day. Then, after filtering through filter cloth and centrifuging, the residue and the filtrate were separated. The separated filtrate was concentrated under reduced pressure to 1/10 the volume of the purified water. Then, after adding ethanol of 4 times the volume of the concentrate in a dropwise manner, the product was dried with hot air to obtain 70 g of a mixture of ginseng polysaccharide and green tea polysaccharide (salt-parched mixed polysaccharide).

[Example 2] Preparation of Scorched Mixed Polysaccharide 50 wt % of dried ginseng and 50 wt % of primarily processed (panned) green tea were carbonized at 270° C. When the color turned black, heating was stopped and the product was cooled at room temperature. 1 kg of the processed mixture of ginseng and green tea was pulverized using a mixer. After adding 10 L of purified water and extracting 3 times under reflux, the resulting extract was settled at 15° C. for a day. Then, after filtering through filter cloth and centrifuging, the residue and the filtrate were separated. The separated filtrate was concentrated under reduced pressure to 1/10 the volume of the purified water. Then, after adding ethanol of 4 times the volume of the concentrate in a dropwise manner, the product was dried with hot air to obtain 72 g of a mixture of ginseng polysaccharide and green tea polysaccharide (scorched mixed polysaccharide).

[Example 3] Preparation of Vinegar-Parched Mixed Polysaccharide 250 g of vinegar was sufficiently absorbed in a mixture of 50 wt % of dried ginseng and 50 wt % of primarily processed (panned) green tea. After parching at 130° C. for 40 minutes, the product was dried in the shade. 1 kg of the processed mixture of ginseng and green tea was pulverized using a mixer. After adding 10 L of purified water and extracting 3 times under reflux, the resulting extract was settled at 15° C. for a day. Then, after filtering through filter cloth and centrifuging, the residue and the filtrate were separated. The separated filtrate was concentrated under reduced pressure to 1/10 the volume of the purified water. Then, after adding ethanol of 4 times the volume of the concentrate in a dropwise manner, the product was dried with hot air to obtain 70 g of a mixture of ginseng polysaccharide and green tea polysaccharide (vinegar-parched mixed polysaccharide).

[Example 4] Preparation of Liquor-Steamed Mixed Polysaccharide

A mixture of 50 wt % of dried ginseng and 50 wt % of primarily processed (panned) green tea was soaked in huangjiu, steamed for 1 hour and 20 minutes and then dried in the shade. 1 kg of the processed mixture of ginseng and green tea was pulverized using a mixer. After adding 10 L of purified water and extracting 3 times under reflux, the resulting extract was settled at 15° C. for a day. Then, after filtering through filter cloth and centrifuging, the residue and the filtrate were separated. The separated filtrate was concentrated under reduced pressure to 1/10 the volume of the purified water. Then, after adding ethanol of 4 times the volume of the concentrate in a dropwise manner, the product was dried with hot air to obtain 77 g of a mixture of ginseng polysaccharide and green tea polysaccharide (liquor-steamed mixed polysaccharide).

[Example 5] Preparation of Ginger-Parched Mixed Polysaccharide

Fresh ginger was triturated and, after mixing with water of 2 times the volume, the mixture was squeezed. This procedure was repeated 2-3 times to prepare ginger juice. After spraying the ginger juice (10-15 wt % based on ginseng) to a mixture of 50 wt % of dried ginseng and 50 wt % of primarily processed (panned) green tea, the mixture soaked with the ginger juice was parched at 140° C. for 40 minutes and then dried in the shade. 1 kg of the processed mixture of ginseng and green tea was pulverized using a mixer. After adding 10 L of purified water and extracting 3 times under reflux, the resulting extract was settled at 15° C. for a day. Then, after filtering through filter cloth and centrifuging, the residue and the filtrate were separated. The separated filtrate was concentrated under reduced pressure to 1/10 the volume of the purified water. Then, after adding ethanol of 4 times the volume of the concentrate in a dropwise manner, the product was dried with hot air to obtain 70 g of a mixture of ginseng polysaccharide and green tea polysaccharide (ginger-parched mixed polysaccharide).

[Example 6] Preparation of Honey-Parched Mixed Polysaccharide

After sufficiently absorbing honey (20-30 wt % based on ginseng) into a mixture of 50 wt % of dried ginseng and 50 wt % of primarily processed (panned) green tea, the mixture was parched at 130° C. for 40 minutes and then dried in the shade. 1 kg of the processed mixture of ginseng and green tea was pulverized using a mixer. After adding 10 L of purified water and extracting 3 times under reflux, the resulting extract was settled at 15° C. for a day. Then, after filtering through filter cloth and centrifuging, the residue and the filtrate were separated. The separated filtrate was concentrated under reduced pressure to 1/10 the volume of the purified water. Then, after adding ethanol of 4 times the volume of the concentrate in a dropwise manner, the product was dried with hot air to obtain 75 g of a mixture of ginseng polysaccharide and green tea polysaccharide (honey-parched mixed polysaccharide).

[Test Example 1] Measurement of Collagenase Expression Inhibiting Effect

The collagenase production inhibiting activity of the substances of Comparative Examples and Examples was compared with tocopherol and EGCG as control substances.

Human fibroblasts were seeded onto a 96-well plate holding Dulbecco's modified Eagle's medium (DMEM) comprising 2.5% fetal bovine serum, with 5,000 cells/well, and cultured until ~90% confluency. The cells were further cultured in serum-free DMEM for 24 hours and treated with the mixture of oriental herbal medicine processed ginseng polysaccharide and green tea polysaccharide prepared in Comparative Examples 1-5 and Examples 1-6 at $10^{-4}$ M in serum-free DMEM for 24 hours. Then the cell culture was collected.

The degree of collagenase production from the collected cell culture was measured using a commercially available collagenase kit (Amersham Pharmacia, USA). First, the cell culture was added to a 96-well plate on which primary collagenase antibody was uniformly coated and antigen-antibody reaction was performed for 3 hours in a constant-temperature incubator.

3 hours later, secondary collagen antibody having a chromophore bonded thereto was added to the 96-well plate and reaction was performed for 15 minutes. 15 minutes later, a color developing agent was added to induce color development at room temperature for 15 minutes. Then, 1 M sulfuric acid was added to stop the reaction (color development). The 96-well plate exhibited yellow color and the degree of yellowness varied depending on the progress of the reaction.

Absorbance was measured at 405 nm using a spectrophotometer and the expression level of collagenase was calculated according to Equation 1. The expression level was calculated with respect to the non-treated control group.

Expression level of collagenase (%)=100−{(Absorbance of cells treated with substances of Comparative Example or Example÷Absorbance of control)×100} [Equation 1]

The collagenase expression inhibiting effect of the test substances in human fibroblasts as the expression level of collagenase is shown in Table 1 relative to the non-treated group as 100.

TABLE 1

| Substances | Expression level of collagenase (%) |
| --- | --- |
| Non-treated | 100 |
| Tocopherol (positive control) | 76 |
| EGCG (positive control) | 63 |
| Comparative Example 1 | 79 |
| Comparative Example 2 | 77 |
| Comparative Example 3 | 77 |
| Comparative Example 4 | 74 |
| Comparative Example 5 | 77 |
| Example 1 | 66 |
| Example 2 | 67 |
| Example 3 | 66 |
| Example 4 | 64 |
| Example 5 | 69 |
| Example 6 | 64 |

It was confirmed that the mixtures of oriental herbal medicine processed ginseng extract and oriental herbal medicine processed green tea extract according to the present disclosure can inhibit the expression of collagenase in vitro.

Also, as seen from Table 1, Examples 1-6 comprising both the oriental herbal medicine processed extracts showed better collagenase inhibiting effect than Comparative Examples. In particular, they exhibited better collagenase inhibiting effect than Comparative Example 5. In addition, the collagenase expression inhibiting effect of Examples 1-6 was even better than that of the positive control tocopherol.

[Test Example 2] Test of Procollagen Production Promoting Effect

The procollagen production promoting activity of the substances of Comparative Examples and Examples was compared with that of vitamin C.

Human fibroblasts were seeded onto a 96-well plate holding Dulbecco's modified Eagle's medium (DMEM) comprising 2.5% fetal bovine serum, with 5,000 cells/well, and cultured until ~90% confluency. The cells were further cultured in serum-free DMEM for 24 hours and treated with the mixture of oriental herbal medicine processed ginseng polysaccharide and green tea polysaccharide prepared in Comparative Examples 1-5 and Examples 1-6 and vitamin C dissolved to $10^{-4}$ M in serum-free DMEM for 24 hours. 24 hours later, the amount of free procollagen was measured using the procollagen type-1 C-peptide EIA kit (MK101, Takara, Japan).

The level of procollagen production is given in Table 2 relative to the non-treated group as 100.

TABLE 2

| Substances | Level of procollagen production (%) |
| --- | --- |
| Non-treated | 100 |
| Vitamin C | 121 |
| Comparative Example 1 | 110 |
| Comparative Example 2 | 106 |
| Comparative Example 3 | 111 |
| Comparative Example 4 | 108 |
| Comparative Example 5 | 108 |
| Example 1 | 119 |
| Example 2 | 119 |
| Example 3 | 120 |
| Example 4 | 123 |
| Example 5 | 118 |
| Example 6 | 122 |

The higher the level of procollagen production, the higher the production level of collagen, allowing prevent of skin wrinkle formation.

It was confirmed that the substances of Examples 1-6 promote the production of procollagen in vitro and the effect was comparable to that of vitamin C which is known as essential in collagen synthesis. In particular, the substances of Examples 1-6 showed much superior effect of promoting procollagen production as compared to Comparative Examples 1-5.

[Test Example 3] Test of Human Keratinocyte Differentiation Inducing Effect

The skin barrier function and skin moisturizing ability of the substances of Comparative Examples and Examples were evaluated by measuring absorbance.

Primarily cultured human keratinocytes (acquired from Dr. N. E. Fusenig, Deutsches Krebsforschungszentrum, Heidelberg, Germany) were attached to the bottom of a culture flask and cultured for 5 days until ~70-80% confluency after adding test substances as described in Table 3. The cells were harvested, washed with phosphate buffered saline (PBS), sonicated for 3 minutes after adding 1 mL of 10 mM Tris-HCl buffer (pH 7.4) comprising 2% sodium dodecyl sulfate (SDS) and 20 mM dithiothreitol (DTT), and then boiled for 10 minutes. Subsequently, after centrifuging at 1200 rpm for 30 minutes, the resulting pellets were resuspended in 1 mL of PBS and absorbance was measured at 340 nm. Separately from this, some of the solution was taken after the sonication and protein content was measured as a reference for a measure of cell differentiation. A low-calcium (0.03 mM) group and a high-calcium (1.2 mM) group were used as negative and positive groups, respectively. The substances of Comparative Examples 1-5 and Examples 1-6 were added to the low-calcium group as test groups. The test result is shown in Table 3.

TABLE 3

|  | Concentration | Keratinocyte differentiating ability (%) |
|---|---|---|
| Controls | Low $Ca^{2+}$ (0.03 mM) | 100 |
|  | High $Ca^{2+}$ (1.2 mM) | 215 |
| Comparative Example 1 | 0.05 ppm | 106 |
|  | 0.1 ppm | 109 |
| Comparative Example 2 | 0.05 ppm | 101 |
|  | 0.1 ppm | 102 |
| Comparative Example 3 | 0.05 ppm | 108 |
|  | 0.1 ppm | 112 |
| Comparative Example 4 | 0.05 ppm | 102 |
|  | 0.1 ppm | 105 |
| Comparative Example 5 | 0.05 ppm | 104 |
|  | 0.1 ppm | 106 |
| Example 1 | 0.05 ppm | 113 |
|  | 0.1 ppm | 125 |
|  | 0.5 ppm | 128 |
| Example 2 | 0.05 ppm | 114 |
|  | 0.1 ppm | 125 |
|  | 0.5 ppm | 128 |
| Example 3 | 0.05 ppm | 112 |
|  | 0.1 ppm | 123 |
|  | 0.5 ppm | 127 |
| Example 4 | 0.05 ppm | 114 |
|  | 0.1 ppm | 125 |
|  | 0.5 ppm | 129 |
| Example 5 | 0.05 ppm | 111 |
|  | 0.1 ppm | 119 |
|  | 0.5 ppm | 124 |
| Example 6 | 0.05 ppm | 114 |
|  | 0.1 ppm | 126 |
|  | 0.5 ppm | 131 |

It was confirmed that the mixtures of oriental herbal medicine processed extracts of Examples 1-6 promote differentiation of keratinocytes from the measurement of the amount of cornified envelopes (CE) produced during the differentiation. In addition, it was confirmed that the mixtures of oriental herbal medicine processed extracts of Examples exhibit much superior effect of inducing differentiation of keratinocytes as compared to Comparative Examples. Accordingly, it can be seen that the composition of the present disclosure exhibits better effect of enhancing skin barrier function and moisturizing skin.

[Test Example 4] Measurement of Filaggrin Expression Through RT-PCR Analysis

The expression level of filaggrin was measured to evaluate the skin moisturizing ability of the substances of Comparative Examples and Examples.

Human keratinocyte HaCaT cell line was acquired from Dr. N. E. Fusenig of the Deutsches Krebsforschungszentrum. $1\times10^5$ cells were distributed onto a 60 mm culture dish. After culturing for a day, the cells were treated with the test substances as described in Table 4 and then cultured for 24 hours. Total RNA was extracted from the cultured cells using TRIzol (Gibco Laboratories, USA) and reverse transcription polymerase chain reaction (RT-PCR) analysis was performed using a one-step RNA PCR kit (AMV; Takara Bio Inc., Japan). Primers for filaggrin (Bioneer, Korea) were used and expression level was compared using β-actin as internal control. The result is given in Table 4 relative to the control group as 100.

TABLE 4

|  | Concentration | Filaggrin production (%) |
|---|---|---|
| Non-treated control | — | 100 |
| Comparative Example 1 | 0.05 ppm | 110 |
|  | 0.1 ppm | 116 |
| Comparative Example 2 | 0.05 ppm | 115 |
|  | 0.1 ppm | 126 |
| Comparative Example 3 | 0.05 ppm | 108 |
|  | 0.1 ppm | 115 |
| Comparative Example 4 | 0.05 ppm | 115 |
|  | 0.1 ppm | 128 |
| Comparative Example 5 | 0.05 ppm | 113 |
|  | 0.1 ppm | 120 |
| Example 1 | 0.05 ppm | 122 |
|  | 0.1 ppm | 162 |
|  | 0.5 ppm | 200 |
| Example 2 | 0.05 ppm | 120 |
|  | 0.1 ppm | 157 |
|  | 0.5 ppm | 195 |
| Example 3 | 0.05 ppm | 122 |
|  | 0.1 ppm | 160 |
|  | 0.5 ppm | 198 |
| Example 4 | 0.05 ppm | 126 |
|  | 0.1 ppm | 168 |
|  | 0.5 ppm | 204 |
| Example 5 | 0.05 ppm | 119 |
|  | 0.1 ppm | 153 |
|  | 0.5 ppm | 194 |
| Example 6 | 0.05 ppm | 128 |
|  | 0.1 ppm | 166 |
|  | 0.5 ppm | 208 |

As seen from Table 4, it was confirmed that the substances of Examples 1-6 promote the expression of filaggrin in keratinocytes. In particular, the substances of Examples 1-6 exhibited remarkably superior effect of promoting the expression of filaggrin as compared to the substances of Comparative Examples 1-5. Accordingly, it can be seen that the composition of the present disclosure is effective in promoting production of natural skin moisturizing factors and strengthening skin moisturizing ability.

[Test Example 5] Measurement of Skin Moisturizing Effect

Nourishing creams Exs. 1-6 (Table 5) and Comp. Exs. 1-5 (Table 6) were prepared as described in Table 5 and Table 6. The unit of the ingredients is wt %.

TABLE 5

| Ingredients | Ex. 1 | Ex. 2 | Ex. 3 | Ex. 4 | Ex. 5 | Ex. 6 |
|---|---|---|---|---|---|---|
| Purified water | To 100 | To 100 | To 100 | To 100 | To 100 | To 100 |
| Example 1 | 0.1 | — | — | — | — | — |
| Example 2 | — | 0.1 | — | — | — | — |
| Example 3 | — | — | 0.1 | — | — | — |
| Example 4 | — | — | — | 0.1 | — | — |
| Example 5 | — | — | — | — | 0.1 | — |
| Example 6 | — | — | — | — | — | 0.1 |
| Hydrogenated vegetable oil | 1.50 | 1.50 | 1.50 | 1.50 | 1.50 | 1.50 |
| Stearic acid | 0.60 | 0.60 | 0.60 | 0.60 | 0.60 | 0.60 |
| Glycerol stearate | 1.00 | 1.00 | 1.00 | 1.00 | 1.00 | 1.00 |
| Stearyl alcohol | 2.00 | 2.00 | 2.00 | 2.00 | 2.00 | 2.00 |
| Polyglyceryl-10 pentastearate + behenyl alcohol + sodium stearoyl lactylate | 1.00 | 1.00 | 1.00 | 1.00 | 1.00 | 1.00 |
| Arachidyl behenyl alcohol + arachidyl glucoside | 1.00 | 1.00 | 1.00 | 1.00 | 1.00 | 1.00 |
| Cetearyl alcohol + cetearyl glucoside | 2.00 | 2.00 | 2.00 | 2.00 | 2.00 | 2.00 |
| PEG-100 stearate + glycerol oleate + propylene glycol | 1.50 | 1.50 | 1.50 | 1.50 | 1.50 | 1.50 |
| Caprylic/capric triglyceride | 11.00 | 11.00 | 11.00 | 11.00 | 11.00 | 11.00 |
| Cyclomethicone | 6.00 | 6.00 | 6.00 | 6.00 | 6.00 | 6.00 |
| Preservative + flavor | adequate | adequate | adequate | adequate | adequate | adequate |
| Triethanolamine | 0.1 | 0.1 | 0.1 | 0.1 | 0.1 | 0.1 |

TABLE 6

| Ingredients | Comp. Ex. 1 | Comp. Ex. 2 | Comp. Ex. 3 | Comp. Ex. 4 | Comp. Ex. 5 |
|---|---|---|---|---|---|
| Purified water | To 100 | To 100 | To 100 | To 100 | To 100 |
| Comparative Example 1 | 0.1 | — | — | — | — |
| Comparative Example 2 | — | 0.1 | — | — | — |
| Comparative Example 3 | — | — | 0.1 | — | — |
| Comparative Example 4 | — | — | — | 0.1 | — |
| Comparative Example 5 | — | — | — | — | 0.1 |
| Hydrogenated vegetable oil | 1.50 | 1.50 | 1.50 | 1.50 | 1.50 |
| Stearic acid | 0.60 | 0.60 | 0.60 | 0.60 | 0.60 |
| Glycerol stearate | 1.00 | 1.00 | 1.00 | 1.00 | 1.00 |
| Stearyl alcohol | 2.00 | 2.00 | 2.00 | 2.00 | 2.00 |
| Polyglyceryl-10 pentastearate + behenyl alcohol + sodium stearoyl lactylate | 1.00 | 1.00 | 1.00 | 1.00 | 1.00 |
| Arachidyl behenyl alcohol + arachidyl glucoside | 1.00 | 1.00 | 1.00 | 1.00 | 1.00 |
| Cetearyl alcohol + cetearyl glucoside | 2.00 | 2.00 | 2.00 | 2.00 | 2.00 |
| PEG-100 stearate + glycerol oleate + propylene glycol | 1.50 | 1.50 | 1.50 | 1.50 | 1.50 |
| Caprylic/capric triglyceride | 11.00 | 11.00 | 11.00 | 11.00 | 11.00 |
| Cyclomethicone | 6.00 | 6.00 | 6.00 | 6.00 | 6.00 |
| Preservative + flavor | adequate | adequate | adequate | adequate | adequate |
| Triethanolamine | 0.1 | 0.1 | 0.1 | 0.1 | 0.1 |

To evaluate the skin moisturizing effect of the substances of Examples 1-6, test was performed as follows using the nourishing creams of Exs. 1-6 and Comp. Exs. 1-5 described in Table 5 and Table 6. 110 healthy women in their 30s were grouped into 11 groups, with 10 per each group, and were asked to apply the nourishing creams of Exs. 1-6 and Comp. Exs. 1-5 for 4 weeks, twice a day, under the condition of 24-26° C. and 75% humidity. Water content in skin was measured using a corneometer prior to the application, 1, 2 and 4 weeks after the commencement of application and 2 weeks after the stopping of the application (6 weeks later) under constant-temperature, constant-humidity condition (24° C., 40% RH). The increase in water content relative to the value prior to the application is given in Table 7 as percentage.

TABLE 7

| | Increase in water content (%) | | | |
|---|---|---|---|---|
| Test result | 1 week later | 2 weeks later | 4 weeks later | 6 weeks later |
| Ex. 1 | 32 | 40 | 40 | 32 |
| Ex. 2 | 31 | 39 | 40 | 30 |
| Ex. 3 | 31 | 39 | 39 | 31 |
| Ex. 4 | 33 | 40 | 40 | 32 |
| Ex. 5 | 31 | 38 | 38 | 31 |
| Ex. 6 | 34 | 41 | 40 | 33 |
| Comp. Ex. 1 | 30 | 32 | 32 | 18 |
| Comp. Ex. 2 | 30 | 33 | 34 | 21 |
| Comp. Ex. 3 | 32 | 34 | 34 | 23 |
| Comp. Ex. 4 | 31 | 33 | 33 | 22 |
| Comp. Ex. 5 | 31 | 33 | 33 | 22 |

As seen from Table 7, the nourishing creams of Exs. 1-6 comprising the oriental herbal medicine processed extracts of the present disclosure resulted in remarkably increased water content in skin as compared to Comp. Exs. 1-5. Since the water content measured 2 weeks after the stopping of the application, i.e. 6 weeks later, was comparable to that 1-2 weeks after the commencement of application, it was confirmed that the skin moisturizing effect of Exs. 1-6 is maintained for a predetermined time even after the application of the test substance is stopped. Accordingly, it can be seen that the composition of the present disclosure can provide improved skin moisturizing effect.

Hereinafter, the present disclosure will be described in detail through preparation examples. However, the following formulation examples are for illustrative purposes only and it will be apparent to those of ordinary skill in the art that the scope of the present disclosure is not limited by the formulation examples.

[Preparation Example 1] Soft Capsule 150 mg of oriental herbal medicine processed ginseng extract, 150 mg of oriental herbal medicine processed green tea extract, 2 mg of palm oil, 8 mg of hydrogenated palm oil, 4 mg of yellow beeswax and 6 mg of lecithin were mixed and filled in capsules, with 400 mg per capsule.

[Preparation Example 2] Tablet 150 mg of oriental herbal medicine processed ginseng extract, 150 mg of oriental herbal medicine processed green tea extract, 100 mg of glucose, 50 mg of red ginseng extract, 96 mg of starch and 4 mg of magnesium stearate were mixed and 40 mg of 30% ethanol was added to form granules. The granules were dried at 60° C. and processed into tablets.

[Preparation Example 3] Granule 150 mg of oriental herbal medicine processed ginseng extract, 150 mg of oriental herbal medicine processed green tea extract, 100 mg of glucose, 50 mg of red ginseng extract and 600 mg of starch were mixed and 100 mg of 30% ethanol was added to form granules. The granules were filled in pouches, with 1 g per pouch.

[Preparation Example 4] Softening Lotion (Skin Lotion)

Softening lotion was prepared according to a commonly employed method with the composition described in Table 8.

TABLE 8

| Ingredients | Contents (wt %) |
|---|---|
| Oriental herbal medicine processed ginseng and green tea extracts (ginseng:green tea = 1:1) | 0.2 |
| Glycerin | 3.0 |
| Butylene glycol | 2.0 |
| Propylene glycol | 2.0 |
| Carboxyvinyl polymer | 0.1 |
| PEG-12 nonyl phenyl ether | 0.2 |
| Polysorbate 80 | 0.4 |
| Ethanol | 10.0 |
| Triethanolamine | 0.1 |
| Preservative, pigment and fragrance | adequate |
| Purified water | balance |

[Preparation Example 5] Nourishing Lotion (Milk Lotion)

Nourishing lotion was prepared according to a commonly employed method with the composition described in Table 9.

TABLE 9

| Ingredients | Contents (wt %) |
|---|---|
| Oriental herbal medicine processed ginseng and green tea extracts (ginseng:green tea = 1:1) | 1.0 |
| Glycerin | 3.0 |
| Butylene glycol | 3.0 |
| Propylene glycol | 3.0 |
| Carboxyvinyl polymer | 0.1 |
| Beeswax | 4.0 |
| Polysorbate 60 | 1.5 |
| Caprylic/capric triglyceride | 5.0 |
| Squalane | 5.0 |
| Sorbitan sesquioleate | 1.5 |
| Liquid paraffin | 0.5 |
| Cetearyl alcohol | 1.0 |
| Triethanolamine | 0.2 |
| Preservative, pigment and fragrance | adequate |
| Purified water | balance |

[Preparation Example 6] Nourishing Cream

Nourishing cream was prepared according to a commonly employed method with the composition described in Table 10.

TABLE 10

| Ingredients | Contents (wt %) |
|---|---|
| Oriental herbal medicine processed ginseng and green tea extracts (ginseng:green tea = 1:1) | 2.0 |
| Glycerin | 3.0 |
| Butylene glycol | 3.0 |
| Liquid paraffin | 7.0 |
| β-Glucan | 7.0 |
| Carbomer | 0.1 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Triethanolamine | 0.1 |
| Preservative, pigment and fragrance | adequate |
| Purified water | balance |

[Preparation Example 7] Massage Cream

Massage cream was prepared according to a commonly employed method with the composition described in Table 11.

TABLE 11

| Ingredients | Contents (wt %) |
|---|---|
| Oriental herbal medicine processed ginseng and green tea extracts (ginseng:green tea = 1:1) | 3.0 |
| Glycerin | 8.0 |
| Butylene glycol | 4.0 |
| Liquid paraffin | 45.0 |
| β-Glucan | 7.0 |

TABLE 11-continued

| Ingredients | Contents (wt %) |
| --- | --- |
| Carbomer | 0.1 |
| Caprylic/capric triglyceride | 3.0 |
| Beeswax | 4.0 |
| Cetearyl glucoside | 1.5 |
| Sorbitan sesquioleate | 0.9 |
| Vaseline | 3.0 |
| Paraffin | 1.5 |
| Preservative, pigment and fragrance | adequate |
| Purified water | balance |

[Preparation Example 8] Pack

Pack was prepared according to a commonly employed method with the composition described in Table 12.

TABLE 12

| Ingredients | Contents (wt %) |
| --- | --- |
| Oriental herbal medicine processed *ginseng* and green tea extracts (*ginseng*:green tea = 1:1) | 0.2 |
| Glycerin | 4.0 |
| Polyvinyl alcohol | 15.0 |
| Hyaluronic acid extract | 5.0 |
| β-Glucan | 7.0 |
| Allantoin | 0.1 |
| Nonyl phenyl ether | 0.4 |
| Polysorbate 60 | 1.2 |
| Ethanol | 6.0 |
| Preservative, pigment and fragrance | adequate |
| purified water | balance |

[Preparation Example 9] Ointment

Ointment was prepared according to a commonly employed method with the composition described in Table 13.

TABLE 13

| Ingredients | Contents (wt %) |
| --- | --- |
| Oriental herbal medicine processed *ginseng* and green tea extracts (*ginseng*:green tea = 1:1) | 0.2 |
| Glycerin | 8.0 |
| Butylene glycol | 4.0 |
| Liquid paraffin | 15.0 |
| β-Glucan | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Preservative, pigment and fragrance | adequate |
| Purified water | balance |

While the exemplary embodiments have been shown and described, it will be understood by those skilled in the art that various changes in form and details may be made thereto without departing from the spirit and scope of this disclosure as defined by the appended claims. In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

The invention claimed is:

1. A composition comprising one or more mixture of a ginseng extract and a green tea extract processed by an oriental herbal medicine processing selected from a group consisting of: a mixture of salt-parched ginseng polysaccharide and salt-parched green tea polysaccharide; a mixture of scorched ginseng polysaccharide and scorched green tea polysaccharide; a mixture of vinegar-parched ginseng polysaccharide and vinegar-parched green tea polysaccharide; a mixture of liquor-steamed ginseng polysaccharide and liquor-steamed green tea polysaccharide; a mixture of ginger-parched ginseng polysaccharide and ginger-parched green tea polysaccharide; and a mixture of honey-parched ginseng polysaccharide and honey-parched green tea polysaccharide, wherein the mixture of salt-parched ginseng polysaccharide and salt-parched green tea polysaccharide is prepared by extracting a mixture of salt, ginseng and green tea; the mixture of scorched ginseng polysaccharide and scorched green tea polysaccharide is prepared by scorching and extracting a mixture of ginseng and green tea; the mixture of vinegar-parched ginseng polysaccharide and vinegar-parched green tea polysaccharide is prepared by extracting a mixture of vinegar, ginseng and green tea; the mixture of liquor-steamed ginseng polysaccharide and liquor-steamed green tea polysaccharide is prepared by extracting a mixture of liquor, ginseng and green tea; the mixture of ginger-parched ginseng polysaccharide and ginger-parched green tea polysaccharide is prepared by extracting a mixture of ginger, ginseng and green tea; and the mixture of honey-parched ginseng polysaccharide and honey-parched green tea polysaccharide is prepared by extracting a mixture of honey, ginseng and green tea, wherein a weight ratio of the oriental herbal medicine processed ginseng extract and the oriental herbal medicine processed green tea extract is 0.1-10:1.

2. The composition according to claim 1, wherein the composition comprises 0.001-10 wt % of the oriental herbal medicine processed ginseng extract and the oriental herbal medicine processed green tea extract, respectively, based on the total weight of the composition.

3. The composition according to claim 1, wherein the composition is a cosmetic composition.

4. The composition according to claim 1, wherein the composition is a pharmaceutical composition.

5. A method for skin anti-aging, which comprises administering the composition according to claim 1 to a subject in need of skin anti-aging.

6. The method according to claim 5, wherein the composition inhibits formation of skin wrinkles or improves skin wrinkles.

7. The method according to claim 5, wherein the composition inhibits expression of collagenase.

8. A method for moisturizing skin, which comprises administering the composition according to claim 1 to a subject in need of moisturizing skin.

* * * * *